(12) United States Patent
Sorge et al.

(10) Patent No.: US 8,496,950 B2
(45) Date of Patent: Jul. 30, 2013

(54) MIXTURE CONTAINING MENTHOL

(75) Inventors: Klaus Sorge, Holzminden (DE); Hubert Loges, Höxter (DE); Arnold Machinek, Holzminden (DE); Ulrike Simchen, Holzminden (DE); Horst Surburg, Holzminden (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 13/302,705

(22) Filed: Nov. 22, 2011

(65) Prior Publication Data
US 2012/0128744 A1 May 24, 2012

Related U.S. Application Data

(60) Provisional application No. 61/416,941, filed on Nov. 24, 2010.

(30) Foreign Application Priority Data

Nov. 24, 2010 (EP) ...................................... 10192468

(51) Int. Cl.
*A61K 8/02* (2006.01)
(52) U.S. Cl.
USPC .......................................................... 424/401
(58) Field of Classification Search
None
See application file for complete search history.

(56) References Cited

U.S. PATENT DOCUMENTS

| 4,564,462 | A  | * | 1/1986 | Watanabe et al. | .............. | 510/152 |
| 4,931,283 | A  | * | 6/1990 | Tsuk | .............................. | 424/449 |
| 6,897,195 | B2 | * | 5/2005 | Su et al. | ............................. | 512/1 |
| 7,138,394 | B2 | * | 11/2006 | Schwarz et al. | ........... | 514/226.5 |
| 7,381,834 | B1 | * | 6/2008 | Erman et al. | ................... | 560/188 |
| 7,482,378 | B2 | * | 1/2009 | Erman et al. | ................... | 514/613 |
| 2004/0018954 | A1 | * | 1/2004 | Su et al. | ............................. | 512/1 |
| 2004/0063794 | A1 | * | 4/2004 | Schwarz et al. | .............. | 514/692 |
| 2005/0025795 | A1 | * | 2/2005 | DeLong et al. | ............... | 424/405 |
| 2005/0265930 | A1 | * | 12/2005 | Erman et al. | ..................... | 424/49 |
| 2006/0211688 | A1 | * | 9/2006 | Schwarz et al. | ........... | 514/226.5 |
| 2006/0241175 | A1 | * | 10/2006 | Schwarz et al. | .............. | 514/458 |
| 2008/0085247 | A1 | * | 4/2008 | Langner et al. | ................. | 424/49 |
| 2008/0317923 | A1 | * | 12/2008 | Ley et al. | ...................... | 426/535 |
| 2009/0123392 | A1 | * | 5/2009 | Braun et al. | .................... | 424/47 |

FOREIGN PATENT DOCUMENTS

JP 2010-051246 A 3/2010
WO WO-2007/115593 A1 10/2007

OTHER PUBLICATIONS

Elka Touitou et al. in: Chirality in Drug Design and Development. 2005 (ed. I.K. Reddy and R. Mehvar). Chapter 3. Transport of Chiral Molecules Across the Skin:59-90.*
EP Search Report in EP Application No. 10192468.6 (Aug. 4, 2011).

* cited by examiner

*Primary Examiner* — Robert A Wax
*Assistant Examiner* — Olga V Tcherkasskaya
(74) *Attorney, Agent, or Firm* — Novak Druce Connolly Bove + Quigg LLP

(57) ABSTRACT

The present invention relates to d,l-menthol and optionally additionally l-menthol-containing mixtures, which are liquid at normal pressure and a temperature of 20° C. or higher. The present invention further relates to products that comprise such a mixture or that are preparable by mixing or contacting such a mixture with further ingredients, and novel processes for preparing menthol-containing products.

20 Claims, No Drawings

MIXTURE CONTAINING MENTHOL

CROSS-REFERENCE TO RELATED APPLICATIONS

This application claims priority under 35 U.S.C. §119(e) to U.S. Provisional Application No. 61/416,941, filed Nov. 24, 2010, and claims priority under 35 U.S.C. §119(a) to EP Application No. 10,192,468.6, filed on Nov. 24, 2010, the entire contents of which is hereby incorporated by reference.

The present invention relates primarily to a novel mixture, which comprises or consists of, relative to the total weight of the mixture, racemic d,l-menthol and optionally additionally l-menthol, in a total amount from 72.0 through 85.0 wt. %,
d,l-isomenthol in an amount from 7.5 through 20.0 wt. %,
a first alkylene diol and optionally one or a plurality of further alkylene diols in a total amount from 7.0 through 11.0 wt. %,
further ingredients in a total amount from 0 through 2.0 wt. %, and is liquid at a pressure of 101325 Pa, also called "normal pressure" hereinafter, and a temperature of 20° C. or higher.

The present invention further relates to products which (i) comprise a mixture according to the invention and further ingredients or (ii) are preparable by mixing or contacting a mixture according to the invention with further ingredients, wherein the further ingredients of the product do not contain menthol and/or isomenthol and preferably do not contain an alkylene diol.

The invention further relates to a process for preparing a menthol-containing product, preferably a product according to the invention.

Another aspect of the present invention relates to the use of d,l-isomenthol mixed with a first alkylene diol and optionally one or a plurality of further alkylene diols as means for lowering the melting point of d,l-menthol, optionally in the presence of additional l-menthol, preferably to a temperature of 20° C. or lower at a pressure of 101325 Pa, i.e. at normal pressure.

Further aspects of the present invention can be seen from the following description, the exemplary embodiments and the claims.

In particular owing to its excellent property of producing a refreshing sensation of coolness on the skin and mucosae, the flavoring material menthol is among the most important substances used for flavoring products, in particular dental hygiene products, chewing gums and refreshing sweets.

Menthol is mainly used in the enantiomerically pure l-form (l-menthol), depending on the desired use, but also as racemate (d,l-form; d,l-menthol). (Pure) l-menthol has a melting point of 42.5° C. The melting point of d,l-menthol is in the range from 34 through 36° C. (Beilstein, Hdb. Org. Chem. 4th ed., 2nd Supplement Vol. VI, Springer Berlin 1944, p. 40; p. 49).

Both from l-menthol, and from d,l-menthol, by rapid cooling it is first possible to produce metastable modifications with lower melting points than those stated above. The (metastable) modifications are, however, transformed e.g. during storage or by thermal treatment, into more stable modifications with higher melting point (F. E. Wright, J. Amer. Chem. Soc. 1917 (39), 1515; M. Kuhnert-Brandstätter, R. Ulmer, L. Langhammer, Arch. Pharm 1974 (307), 497-503).

At ordinary storage temperatures, i.e. in particular at a temperature in the range from 0 through 30° C., l-menthol and d,l-menthol are in the form of crystalline solids.

In the processing of menthol, in particular of l-menthol and d,l-menthol, depending on the use it is often necessary to use menthol in liquid form, rather than in solid, crystalline form. The liquid state of aggregation advantageously permits simpler and more accurate dosing when adding menthol, in particular in the production of flavoring material preparations (e.g. flavor concentrates), and better incorporation into media or pastes that are to be flavored, for the production of flavored products.

For use in liquid form, up until now menthol has often first been melted and then supplied (in liquid form) at elevated temperature. However, this operation requires the use of special equipment and is particularly energy-consuming.

In the flavor materials processing industry there is therefore a need to provide menthol or menthol mixtures that can already be processed in the liquid state at an ambient temperature in the region of 20° C.

Various approaches for this have already been described in the prior art, but these sometimes have considerable drawbacks.

For example, the taking up of menthol in a suitable solvent, in order to obtain a solution that makes it possible to use menthol in liquid form at a desired processing temperature, is well known. However, a drawback of this procedure is that it requires relatively large amounts of solvent. On the one hand, the resultant dilution of menthol reduces its desired effect. On the other hand, in the production of flavoring material preparations (e.g. flavor concentrates) or during incorporation into media or pastes that are to be flavored for the production of flavored products (e.g. toothpastes and chewing gums), it leads to various problems. Thus, the use of quite large amounts of solvent for example sometimes leads to undesirable changes in the fluidity or the viscosity of certain products.

Thus, for example, addition of (only) 10 wt. % of 1,2-propylene glycol, a permitted solvent for food flavorings, to d,l-menthol produces a mixture that is in the form of a solid at normal pressure (101325 Pa) and at a temperature of below 25° C. In order to obtain a mixture that is already liquid at a temperature of 20° C. at normal pressure, it is necessary to increase the amount of 1,2-propylene glycol considerably. This has the drawback, however, that the solvent reduces the sensory properties of menthol to an undesirable extent relative to the starting material, i.e. relative to pure menthol. Moreover, such a high proportion of solvent can lead to problems in the formulation of (finished) products.

Therefore in the flavor materials processing industry there is in particular a need for menthol-containing mixtures that are already liquid at a temperature of 20° C. at normal pressure and whose sensory effect is not, or not substantially, reduced relative to pure menthol, in particular relative to pure l-menthol or d,l-menthol, wherein moreover the proportion of solvent, relative to the total weight of the mixture, is preferably in the region of 10 wt. % or less.

One possibility that is known from the prior art for lowering the melting point of menthol is to use a mixture of different menthol isomers.

For example, it can be seen from the melting diagram of d-menthol and l-menthol (see M. Kuhnert-Brandstätter, R. Ulmer, L. Langhammer, Arch. Pharm 1974 (307), 497-503) that the lowest melting point (eutectic point) that can be obtained by mixing d,l-menthol and l-menthol is approx. 30° C. In comparison, the melting temperature of the pure enantiomers is 42.5° C. The composition at the eutectic point corresponds to a mixture ratio of 68 wt. % l-menthol and 32 wt. % d-menthol, which in its turn corresponds to a mixture ratio of 64 wt. % of (racemic) d,l-menthol and 36 wt. % of (pure) l-menthol.

However, even by adding an amount of solvent of max. 10 wt. % of 1,2-propylene glycol to the composition at the eutectic point (see previous paragraph), according to our own investigations (see below, example 1.3, third mixture) the melting point can only be lowered to 23° C., but not to the desired range of 20° C.

Another approach is described in JP 2008-220048. It is reported there that by adding d-neomenthol to l-menthol it is possible to prevent l-menthol crystallizing out. For this, a proportion of d-neomenthol of about 4 wt. %, relative to the proportion by weight of l-menthol in the composition, is recommended. However, such a procedure has the drawback that the refreshing, cooling effect of menthol is perceptibly impaired by the pronounced earthy-musty note of neomenthol (cf. R. Emberger, R. Hopp, in Topics in Flavor Research, eds. R. G. Berger, S, Nitz, P. Schreier, H. Eichhorn, Marzling-Hangenham 1985, p. 201-218). Therefore addition of d-neomenthol to l-menthol or d,l-menthol is undesirable from sensory considerations.

WO 2007115593 discloses a mixture of menthyl lactate, neomenthol and menthol as cooling or aromatizing agent with a solidification point below +5° C., wherein the weight ratio of neomenthol to menthol is in the range from 1:1.25 through 1:2.5.

US 2004/018954 discloses a composition containing menthol and menthyl lactate, and use thereof as cooling and aromatizing agent. The composition contains menthol and menthyl lactate in a weight ratio in the range from 1:4 through 4:1, and the crystallization point is below an ambient temperature of 25° C.

The primary object to be achieved by the present invention is therefore to provide a menthol-containing mixture that is already in the liquid state at a temperature of 20° C. at normal pressure, wherein the further ingredients of this mixture preferably do not, or at best barely, impair the sensory effect of methanol [sic]. More preferably, such a mixture should be provided in which the proportion of solvent does not have to be so high that the aforementioned problems occur.

Another object to be achieved by the present invention is to provide novel menthol-containing products and a method for preparing a novel menthol-containing product.

Further objects to be achieved in connection with the present invention can be seen from the following description, the accompanying examples and the patent claims.

The primary object to be achieved by the present invention is achieved with a mixture that is liquid at a pressure of 101325 Pa, i.e. at normal pressure, and a temperature of 20° C. or higher, consisting of or comprising racemic d,l-menthol and optionally additionally l-menthol, in a total amount from 72.0 through 85.0 wt. %,
d,l-isomenthol in an amount from 7.5 through 20.0 wt. %,
a first alkylene diol and optionally one or a plurality of further alkylene diols in a total amount from 7.0 through 11.0 wt. %,
further ingredients in a total amount from 0 through 2.0 wt. %, wherein the percentages by weight are relative to the total weight of the mixture.

A mixture according to the invention accordingly comprises both d-menthol and l-menthol, wherein the amount of l-menthol is either an equimolar or an above-equimolar amount relative to the amount of d-menthol.

A mixture according to the invention is (at normal pressure) liquid at a temperature of 20° C. or higher, i.e. both at a temperature of 20° C., and at a higher temperature. In particularly preferred embodiments of a mixture according to the invention (as described in the present text) sometimes even melting points of less than 20° C. are attained. However, this was not to be expected, but rather was particularly surprising, as will be explained in greater detail hereunder.

Isomenthol admittedly has a more suitable profile for sensory purposes than d-neomenthol (see above), but it has melting points that are significantly higher than those of menthol. Thus, the melting temperature of d,l-isomenthol (as contained in a mixture according to the invention) is in the range from 52 through 53° C.; the melting temperature of d-isomenthol is even 82.5° C. (Beilstein, Hdb. Org. Chem. 4th ed., 2nd Supplement Vol. VI, Springer Berlin 1944, p. 51). Therefore it was unexpected that a mixture according to the invention (as described above) comprising 7.5 through 20 wt. % d,l-isomenthol is, at normal pressure, already liquid at a temperature of 20° C. In particular it was not to be expected that the addition of d,l-isomenthol can contribute to lowering the melting point of d,l-menthol and optionally additionally l-menthol-containing mixture to the required extent. For as we established in comparative tests, a mixture of 50 wt. % d,l-menthol and 50 wt. % d,l-isomenthol (without additional solvent) has a melting temperature of 36.5° C. For a mixture of 80 wt. % d,l-menthol and 20 wt. % d,l-isomenthol (without additional solvent), a melting temperature of 34.5° C. was found at normal pressure. The melting temperatures of mixtures of 25 through 50 wt. % l-menthol, 65 through 40 wt. % d,l-menthol and 10 wt. % d,l-isomenthol were, according to our own investigations, also in the range from 33 through 34° C.

It was particularly surprising that the melting point of a mixture containing d,l-menthol and optionally additionally l-menthol could be reduced by adding 7.5 through 20 wt. % d,l-isomenthol and in addition 7.0 through 11 wt. % alkylene diol, so that a mixture (according to the invention) is obtained which, at normal pressure (101325 Pa), is already liquid at a temperature of 20° C. This is surprising since, for example, addition of 10 wt. % of 1,2-propylene glycol to d,l-menthol only leads to a melting point depression of max. 10° C. and an addition of 10 wt. % of 1,2-propylene glycol to a eutectic mixture of d,l-menthol and l-menthol only leads to a melting point depression of max. 7° C. (cf. examples 1.2 and 1.3 given below).

For the mixtures according to the invention (as described in the present text), the melting point is advantageously lowered by about 15° C. or more relative to mixtures of l-menthol (and optionally d,l-menthol) and propylene glycol without additional d,l-isomenthol.

For the purposes of the present invention it is particularly preferable for the amount of d,l-isomenthol relative to the total amount of d,l-menthol and optionally l-menthol to be 5 through 25 wt. %, more preferably 10 through 20 wt. %. In combination with 7.5 through 10 wt. % of alkylene diol, e.g. 1,2-propylene glycol, advantageously a mixture according to the invention is obtained whose melting point is even below 20° C.

For the purposes of the present invention, a mixture according to the invention is particularly preferred wherein the one alkylene diol or one, a plurality of or all of the alkylene diols are selected from the group consisting of alkylene glycols with 2 through 6 carbon atoms.

Particularly preferably, the or one, a plurality of or all of the alkylene diols are selected from the group consisting of ethylene glycol, 1,2-propylene glycol, 1,3-propylene glycol, 1,2-butylene glycol, 1,4-butylene glycol and 1,2-hexylene glycol.

Generally it is preferable if the or one, a plurality of or all of the alkylene diols in the mixture according to the invention are selected from the group consisting of ethylene glycol, propylene glycol and hexylene glycol.

If a mixture according to the invention comprises, along with d,l-menthol, additionally l-menthol, it is particularly preferable if the weight ratio of d,l-menthol to l-menthol is greater than 1:4, preferably greater than 1:2.

According to an particularly preferred aspect of the present invention the proportion by weight of l-menthol, relative to the total weight of d,l-menthol and l-menthol in the mixture, in a mixture according to the invention, is preferably in the range from 0 through 80 wt. %, particularly preferably in the range from 0 through 60 wt. %. More preferably the proportion of l-menthol in a mixture according to the invention, relative to the total weight of the mixture, is in the range from 0 through 51 wt. %.

According to another aspect in connection with the present invention, a mixture is provided, consisting of or comprising a total amount of (racemic) d,l-menthol and optionally additionally (pure) l-menthol in the range from 61 through 89 wt. %, preferably in the range from 71 through 84 wt. %, an amount of d,l-isomenthol in the range from 4 through 24 wt. %, preferably in the range from 6 through 24 wt. %, and a total amount of a first alkylene diol (e.g. 1,2-propylene glycol) and optionally one or a plurality of further alkylene diols in the range from 6 through 19 wt. %, preferably an amount of 1,2-propylene glycol in the range from 6 through 11 wt. %. For preferred embodiments of such a mixture, the foregoing applies correspondingly.

For the purposes of the present invention, a mixture according to the invention (as described above) is particularly suitable that consists of or comprises racemic d,l-menthol in an amount from 72.0 through 85.0 wt. %,
d,l-isomenthol in an amount from 7.5 through 20.0 wt. %,
1,2-propylene glycol in an amount from 7.0 through 11.0 wt. %,
further ingredients in a total amount from 0 through 2.0 wt. %, wherein the percentages by weight are relative to the total weight of the mixture. Said mixture preferably does not comprise any additional (pure) l-menthol along with d,l-menthol.

Another preferred embodiment of the present invention relates to a mixture according to the invention, consisting of or comprising racemic d,l-menthol in an amount from 48 through 57 wt. %
additionally l-menthol in an amount from 21.0 through 32.0 wt. %,
d,l-isomenthol in an amount from 8.0 through 14.0 wt. %,
1,2-propylene glycol in an amount from 7.0 through 11.0 wt. %,
further ingredients in a total amount from 0 through 2.0 wt. %, wherein the percentages by weight are relative to the total weight of the mixture.

According to a preferred embodiment of the present invention a mixture according to the invention does not comprise any further ingredients (0 wt. %), i.e. according to this aspect of the present invention a mixture according to the invention preferably consists of racemic d,l-menthol and optionally additionally pure l-menthol in the aforementioned amount, d,l-isomenthol in the aforementioned amount and one or a plurality of alkylene diols in the aforementioned amount.

The mixtures according to the invention advantageously permit an easily manageable and precise metering in the production of flavoring material preparations, in particular flavor concentrates, and moreover offer better handling during incorporation into media and pastes that are to be flavored. Another advantage of mixtures according to the invention is that these only comprise 11 wt. % or less of alkylene diol, since solvents in larger amounts, as described above, can lead to problems with certain media and pastes or in the formulation of (finished) products.

As shown in comparative tests, another advantage of mixtures according to the invention is that they impart an overall sensory impression that is comparable to pure d,l-menthol.

Accordingly, the mixtures according to the invention are advantageously particularly suitable as an ingredient of flavoring material preparations or as an ingredient of products that are to be flavored. The mixtures according to the invention are suitable in particular for use in flavoring material preparations, in cosmetic preparations and preparations used for nutrition and/or pleasure, in particular those that conventionally contain (crystalline) menthol.

Another aspect of the present invention accordingly relates to a product,
(i) comprising a mixture according to the invention and further ingredients or
(ii) is preparable by mixing or contacting a mixture according to the invention with further ingredients,
wherein the further ingredients of the product do not contain menthol and/or isomenthol and preferably do not contain an alkylene diol.

Preferably the product is selected from the group consisting of flavoring material preparations, cosmetic preparations, preparations used for nutrition and/or pleasure (e.g. tobacco products), preferably preparations ready for consumption or use, in particular beverages and chewable foodstuffs, in particular chewing gums and chewable sweets (e.g. refreshing sweets), oral hygiene products and dental hygiene products, in particular toothpaste and dental-hygiene chewing gums, perfumes (mixtures of odoriferous substances), pharmaceutical and dermatological products, encapsulated menthol-containing preparations, household products.

In pharmaceutical and dermatological products and cosmetic preparations, a mixture according to the invention preferably acts as a penetration enhancer. A penetration enhancer is a substance that improves the entry of an active substance into or passage of an active substance through the skin barrier or portions of the skin barrier, in particular the stratum corneum.

Accordingly, a product according to the invention is, according to a first aspect, preferably a flavoring material preparation, which apart from the mixture according to the invention, comprises, as one or a plurality of further ingredients, one or a plurality of further flavoring materials.

A flavoring material preparation according to the invention is preferably a flavoring material preparation that is used for flavoring oral hygiene products, dental hygiene products and chewing gums.

According to another aspect of the present invention, a product according to the invention, as described above, is preferably a cosmetic preparation, a preparation used for nutrition and/or pleasure. Such a product according to the invention can also contain a flavoring material preparation (according to the invention), which in its turn comprises the mixture according to the invention (as described above). Said product is preferably an oral hygiene product, a dental hygiene product or a chewing gum.

Particularly preferably, a flavoring material preparation (according to the invention) described above has a eucalyptus, a peppermint, a spearmint, a cinnamon, a wintergreen and/or a citrus flavor note.

Flavoring materials (e.g. in a flavoring material preparation according to the invention (as described above)) that can be combined advantageously with a mixture according to the invention are mentioned below:

Flavoring materials that are suitable for use are basically natural raw materials such as extracts and essential oils obtained from plants, or fractions obtained therefrom and substances isolated therefrom, as well as individual flavoring materials obtained synthetically or biotechnologically.

Preferred natural raw materials are selected from the group consisting of: peppermint oils, spearmint oils, Mentha-arvensis oils, anise oils, clove oils, citrus oils, cinnamon bark oils, wintergreen oils, cassia oils, davana oils, spruce needle oils, eucalyptus oils, fennel oils, galbanum oils, ginger oils, chamomile oils, caraway oils, rose oils, geranium oils, sage oils, yarrow oils, star anise oils, thyme oils, juniper berry oils, rosemary oils, angelica root oils, and the fractions of these oils.

Preferred individual compounds, which can be used as further flavoring material or further flavoring materials with a mixture according to the invention, are preferably selected from the group consisting of: anethole, menthone, isomenthone, menthyl acetate, menthofuran, menthyl methyl ether, mint-lactone, eucalyptol, limonene, eugenol, pinene, sabinene hydrate, 3-octanol, carvone, gamma-octalactone, gamma-nonalactone, germacrene-D, viridiflorol, 1,3E,5Z-undecatriene, isopulegol, piperitone, 2-butanone, ethyl formate, 3-octyl acetate, isoamylisovalerate, hexanol, hexanal, cis-3-hexenol, linalool, alpha-terpineol, cis and trans carvyl acetate, p-cymene, thymol, 4,8-dimethyl-3,7-nonadien-2-one, damascenone, damascone, rose oxide, dimethylsulphide, fenchol, acetaldehyde-diethylacetal, cis-4-heptenal, isobutyraldehyde, isovaleraldehyde, cis-jasmone, anisaldehyde, methylsalicylate, myrtenyl acetate, 8-ocimenyl acetate, 2-phenylethyl alcohol, 2-phenylethylisobutyrate, 2-phenylethylisovalerate, cinnamaldehyde, geraniol, nerol. In the case of chiral compounds, the aforementioned flavoring materials can be in the form of racemate, as individual enantiomer or as enantiomer-enriched mixtures.

Additional flavoring materials that are preferably to be used are 1,8-cineol (eucalyptol), menthone, carvone, cinnamaldehyde and/or methylsalicylate.

Naturally, the aforementioned flavoring materials can be used in the form of mixtures of flavorings. Therefore a flavoring material preparation (according to the invention) is preferred that comprises, as further ingredient(s)
eucalyptus flavorings, containing eucalyptol; and/or
peppermint flavorings, containing menthone; and/or
spearmint flavorings, containing carvone; and/or
cinnamon flavorings, containing cinnamaldehyde; and/or
wintergreen flavorings, containing methylsalicylate.

In some cases products according to the invention, in particular flavoring material preparations are preferred that additionally contain flavoring materials that have a sharp taste or produce a sensation of warmth or heat on the skin and mucosae or a tingling or prickling sensation in the oral and pharyngeal cavity, e.g. paprika powder, chilli-pepper powder, extracts of paprika, extracts of pepper, extracts of chilli-pepper, extracts of ginger root, extracts of paradise seeds (*Aframomum melegueta*), extracts of paracress (*jambul oleoresin; Spilanthes acmella*, or *Spilanthes oleracea*), extracts of Japanese pepper (*Xanthoxylum piperitum*), extracts of *Kaempferia galanga*, extracts of *Alpinia galanga*, extracts of water pepper (*Polygonium hydropiper*), capsaicin, dihydrocapsaicin, gingerol, paradol, shogaol, piperine, saanshool-I, saanshool-II, sanshoamide, spilanthol, carboxylic acid-N-vanillyl amides, in particular nonanoic acid-N-vanillyl amide, 2-nonenoic acid amides, in particular 2-nonenoic acid-N-isobutyl amide, 2-nonenoic acid-N-4-hydroxy-3-methoxyphenyl amide, alkyl ethers of 4-hydroxy-3-methoxybenzyl alcohol, in particular 4-hydroxy-3-methoxybenzyl-n-butyl ether, alkyl ethers of 3-hydroxy-4-methoxybenzyl alcohol, alkyl ethers of 3,4-dimethoxybenzyl alcohol, alkyl ethers of 3-ethoxy-4-hydroxybenzyl alcohol, alkyl ethers of 3,4-methylene dioxybenzyl alcohol, acetals of vanillin, acetals of ethylvanillin, acetals of isovanillin, (4-hydroxy-3-methoxyphenyl)acetic acid amides, in particular (4-hydroxy-3-methoxyphenyl)acetic acid-N-n-octyl amide, allyl isothiocyanate, nicotinaldehyde, methylnicotinate, propylnicotinate, 2-butoxyethylnicotinate, benzylnicotinate, 1-acetoxychavicol.

Furthermore, mixtures according to the invention (as described above) can be combined excellently with substances that produce a physiological cooling effect on the skin and/or mucosae.

Accordingly, a product according to the invention preferably additionally contains one or a plurality of (further) substances with a physiological cooling effect. Said further substance or substances with a physiological cooling effect are preferably selected from the group consisting of: menthyl ether (e.g. (l-menthoxy)-1,2-propanediol, (l-menthoxy)-2-methyl-1,2-propanediol, 1-menthyl-methyl ether), menthyl esters (e.g. menthyl formate, menthyl acetate, menthyl isobutyrate, menthyl lactates, preferably L-menthyl lactate, L-menthyl-L-lactate, L-menthyl-D-lactate, menthyl-(2-methoxy)acetate, menthyl-(2-methoxyethoxy)acetate, menthyl pyroglutamate), menthyl carbonates (e.g. menthyl alkyl carbonates, menthyl propylene glycol carbonate, menthyl ethylene glycol carbonate, menthyl glycerol carbonate or mixtures thereof), the semi-esters of menthols with a dicarboxylic acid or derivatives thereof (e.g. mono-menthyl succinate, mono-menthyl glutarate, mono-menthyl malonate, O-menthyl succinic acid ester-N,N-(dimethyl)amide, O-menthyl succinic acid ester amide), menthane-carboxylic acid amides (e.g. menthane-carboxylic acid-N-ethyl amide [WS-3], menthane-carboxylic acid-N-(4-methoxyphenyl)-amide [WS-12], $N^\alpha$-(menthane-carbonyl)glycine ethyl ester [WS-5], menthane-carboxylic acid-N-(4-cyanophenyl) amide, menthane-carboxylic acid-N-(alkoxyalkyl)amides), menthone and menthone derivatives (e.g. menthone ketals such as L-menthone glycerolketal), 2,3-dimethyl-2-(2-propyl)-butanoic acid derivatives (e.g. 2,3-dimethyl-2-(2-propyl)-butanoic acid-N-methyl amide [WS-23]), isopulegol or esters thereof (l-(−)-isopulegol, l-(−)-isopulegol acetate), menthane derivatives (e.g. p-menthane-3,8-diol), cubebol or synthetic or natural mixtures containing cubebol, pyrrolidone derivatives of cycloalkyldione derivatives (e.g. 3-methyl-2(1-pyrrolidinyl)-2-cyclopenten-1-one) or tetrahydropyrimidin-2-ones (e.g. icilin or related compounds, as described in WO 2004/026840), N-(4-cyanomethylphenyl)-p-menthane-carboxamide, N-(2-(pyridin-2-yl) ethyl)-3-p-menthane-carboxamide, acetic acid-2-(methylamino)-2-oxo-, 5-methyl-2-(1-methylethyl)cyclohexyl ester, acetic acid-2-(ethylamino)-2-oxo-, 5-methyl-2-(1-methylethyl)cyclohexyl ester. Substances with a cooling effect based on a menthol skeleton structure are preferable, in particular derivatives of l-menthol.

It is preferable to use one or a plurality of further substances with a physiological cooling effect, which although producing a physiological cooling effect, do not simultaneously produce any or any important gustatory effect. Preferred substances with a physiological cooling effect are therefore selected from the group consisting of: menthyl ether (e.g. (l-menthoxy)-1,2-propanediol, (l-menthoxy)-2-methyl-1,2-propanediol), more-polar menthyl esters (e.g. menthyl lactates, L-menthyl-L-lactate, L-menthyl-D-lactate, menthyl-(2-methoxy)acetate, menthyl-(2-methoxyethoxy)acetate, menthyl pyroglutamates), menthyl carbonates (e.g. menthyl propylene glycol carbonate, menthyl ethylene glycol carbonate, menthyl glycerol carbonate), the semi-esters of menthols with a dicarboxylic acid or derivatives thereof (e.g. mono-menthyl succinate, mono-menthyl glutarate, mono-menthyl malonate, O-menthyl succinic acid ester-N,N-(dimethyl)amide, O-menthyl succinic acid ester amide), menthane-carboxylic acid amides not according to the invention (e.g. menthane-carboxylic acid-N-ethyl amide [WS-3], menthane-carboxylic acid-N-(4-methoxyphenyl)-amide [WS-12], $N^{\alpha}$-(menthane-carbonyl)glycine ethyl ester [WS-5], menthane-carboxylic acid-N-(4-cyanophenyl)amide, menthane-carboxylic acid-N-(alkoxyalkyl)amides), menthone derivatives (e.g. L-menthone glycerolketal), 2,3-dimethyl-2-(2-propyl)-butanoic acid derivatives (e.g. 2,3-dimethyl-2-(2-propyl)-butanoic acid-N-methyl amide), pyrrolidone derivatives of cycloalkyldione derivatives (e.g. 3-methyl-2(1-pyrrolidinyl)-2-cyclopenten-1-one), 2,2,2-trialkylacetic acid amides (e.g. 2,2-diisopropylpropionic acid methyl amides) or tetrahydropyrimidin-2-ones (e.g. icilin, icilin derivatives or related compounds, which are described in WO 2004/026840).

Substances and excipients that a product according to the invention can (additionally) contain are for example:

Preservatives, preferably those mentioned in US 2006/0089413, abrasives, anti-acne agents and agents for reducing sebum, preferably those mentioned in WO 2008/046791, agents against skin ageing, preferably those mentioned in WO 2005/123101, antibacterial agents, anticellulitis agents, antidandruff agents, preferably those mentioned in WO 2008/046795, anti-inflammatory agents, agents preventing irritation, anti-irritants (anti-inflammatory agents, irritation-inhibiting agents and agents preventing irritation), preferably those mentioned in WO 2007/042472 and US 2006/0089413, antimicrobial agents, preferably those mentioned in WO 2005/123101, antioxidants, preferably those mentioned in WO 2005/123101, astringents, antiseptics, antistatic agents, binders, buffers, carriers, preferably those mentioned in WO 2005/123101, chelating agents, preferably those mentioned in WO 2005/123101, cell stimulants, cleansing agents, care agents, depilatory agents, surface active substances, deodorants and antiperspirants, preferably those mentioned in WO 2005/123101, plasticizers, emulsifiers, preferably those mentioned in WO 2005/123101, enzymes, essential oils, preferably those mentioned in US 2008/0070825, insect repellents, preferably those mentioned in WO 2005/123101, fibers, film-forming agents, fixatives, foaming agents, foam stabilizers, antifoaming agents, foam boosters, fungicides, gelling agents and gel-forming agents, preferably those mentioned in WO 2005/123101, hair care agents, hair shaping agents, hair-straightening agents, moisture regulators (hydrating agents, moisturizers and/or humectants), preferably those mentioned in WO 2005/123101, osmolytes, preferably those mentioned in WO 2005/123101, compatible solutes, preferably those mentioned in WO 01/76572 and WO 02/15686, bleaching agents, strengthening agents, stain removers, optical brighteners, impregnating agents, dirt-repelling agents, agents reducing friction, lubricants, moisturizing creams, ointments, opacifiers, plasticizers, covering agents, polishes, gloss agents, polymers, preferably those mentioned in WO 2008/046676, powders, proteins and protein hydrolysates, preferably those mentioned in WO 2005/123101 and WO 2008/046676, refatting agents, abrading agents, skin calmatives, skin cleansing agents, skin care agents, skin healing agents (skin repair agents), preferably containing cholesterol and/or fatty acids and/or ceramides and/or pseudoceramides, and preferably those mentioned in WO 2006/053912, skin lightening agents, preferably those mentioned in WO 2007/110415, skin protectants, skin softening agents, skin cooling agents, preferably those mentioned in WO 2005/123101, skin warming agents, preferably those mentioned in WO 2005/123101, stabilizers, UV-absorbing agents and UV filters, preferably those mentioned in WO 2005/123101, benzylidene-beta-dicarbonyl compounds, preferably those mentioned in WO 2005/107692, alpha-benzoylcinnamic acid nitriles, preferably those mentioned in WO 2006/015954, AhR receptor antagonists, preferably those mentioned in WO 2007/128723 and WO 2007/060256, detergents, fabric softeners, suspending agents, skin tanning agents, preferably those mentioned in WO 2006/045760, thickeners, vitamins, preferably those mentioned in WO 2005/123101, oils, waxes and fats, preferably those mentioned in WO 2005/123101, phospholipids, preferably those mentioned in WO 2005/123101, fatty acids (saturated fatty acids, mono- or polyunsaturated fatty acids, α-hydroxy acids, polyhydroxyfatty acids), preferably those mentioned in WO 2005/123101, liquefiers, dyes and color-protecting agents and pigments, preferably those mentioned in WO 2005/123101, anticorrosive agents, flavorings and flavoring substances and odoriferous substances, preferably those listed in S. Arctander, Perfume and Flavor Chemicals, self-published, Montclair, N.J., 1969 and Surburg, Panten, Common Fragrance and Flavor Materials, 5th edition, Wiley-VCH, Weinheim 2006, in particular those explicitly mentioned in US 2008/0070825, alcohols and polyols, preferably those mentioned in WO 2005/123101, surfactants, preferably those mentioned in WO 2005/123101, animal extracts, yeast extracts, extracts of algae or microalgae, electrolytes, liquefiers, organic solvents, preferably those mentioned in WO 2005/123101, or silicones and silicone derivatives, preferably those mentioned in WO 2008/046676.

Products according to the invention that can be taken orally are also advantageous, e.g. in the form of tablets (e.g. film-coated tablets), sugar-coated tablets, capsules (e.g. gelatin capsules), granules, juices, solutions, emulsions, microemulsions, sprays or products consumable orally in other forms or in the form of foodstuffs, which together with other appropriate active substances contained therein bring about "beauty from inside".

Furthermore, the mixtures according to the invention or the products described above, in particular flavoring material preparations, can be in encapsulated form, wherein they are preferably encapsulated with a solid shell material, which is preferably selected from starch, degraded or chemically or physically modified starch (in particular dextrins and maltodextrins), gelatins, gum arabic, agar-agar, ghatti gum, gellan gum, modified and unmodified celluloses, pullulan, curdlan, carrageenans, alginic acid, alginates, pectin, inulin, xanthan gum and mixtures of two or a plurality of the aforementioned substances.

Preferably the solid shell material is selected from gelatin (porcine, bovine, chicken and/or fish gelatins and mixtures thereof are advantageous, preferably comprising at least one gelatin with a Bloom value greater than or equal to 200, preferably with a Bloom value greater than or equal to 240), maltodextrin (preferably obtained from maize, wheat, tapioca or potato; preferred maltodextrins have a DE value from 10 through 20), modified cellulose (e.g. cellulose ethers), alginates (e.g. Na-alginate), carrageenan (beta, iota, lambda and/ or kappa carrageenan), gum arabic, curdlan and/or agar-agar. Gelatin is preferably used in particular owing to its good availability in different Bloom values.

Seamless gelatin or alginate capsules, the shell of which dissolves very quickly in the mouth or disintegrates on chewing, are particularly preferred, particularly for oral use. They can be produced as described for example in EP 0 389 700, U.S. Pat. No. 4,251,195, U.S. Pat. No. 6,214,376, WO 03/055587 or WO 2004/050069.

As mentioned above, according to one aspect of the present invention, a product according to the invention is preferably a cosmetic preparation. A cosmetic preparation that is preferred according to the invention is a dermatological preparation, which (apart from the mixture according to the invention that it contains) has the usual composition and preferably serves for cosmetic, in particular dermatological light protection, for the treatment, care and cleaning of the skin and/or of the hair or as make-up product in decorative cosmetics. Correspondingly, such preparations can, depending on their structure, be used for example as skin protective cream, day cream or night cream, eye cream, sunscreen or after-sun lotion, nourishing cream, care mask, gel-pads, face lotion, moist care and cleaning wipes, cleansing milk, cleansing soap, foam or shower gel, deodorants, antiperspirants, hair shampoos, hair care agents, hair conditioners, hair colorings, hair styling agents and preferably as emulsion, lotion, milk, fluid, cream, aqueous-dispersion gel, balm, spray, alcoholic or aqueous-alcoholic solution, foam, powder, liquid soap, soap bar, shampoo, roll-on, stick or make-up. In hair treatment agents, use is preferably directed towards the scalp.

For use, the cosmetic preparations according to the invention are applied in sufficient amount, in the usual manner for cosmetics, on the skin and/or the hair.

Correspondingly, cosmetic preparations according to the invention can, depending on their structure, preferably be used as skin care agents, e.g. skin protective cream, day cream or night cream, sunscreen agents, after-sun preparations (e.g. after-sun lotion), care mask, gel-pads, face lotion, moist care and/or impregnating solution, e.g. for cosmetic wipes, cleaning wipes, cleansing soap, foam or shower gel, liquid soap, soap bar, shampoo (e.g. 2-in-1 shampoo, anti-dandruff shampoo, baby shampoo, shampoo for dry scalp, shampoo concentrate), hair care agents, hair conditioners, hair colorings, hair rinse, hair styling agents (e.g. hair gel), deodorants, antiperspirants (e.g. roll-on or stick), shaving preparations (e.g. aftershave balm, pre-shave or aftershave lotion) or as make-up remover.

A cosmetic preparation according to the invention is in the form of an emulsion, lotion, fluid, cream, micro-emulsion, gel (e.g. aqueous or aqueous-dispersion gel), balsam, pump spray, alcoholic or aqueous-alcoholic solution.

Another aspect of the present invention relates to a process for producing a menthol-containing product, preferably a product according to the invention (as described above), comprising the following steps:

provising or preparing a mixture according to the invention (as described above), mixing or contacting the mixture with further ingredients, wherein the further ingredients do not contain menthol and/or isomenthol and preferably do not contain an alkylene diol.

For preferred embodiments of a mixture (according to the invention), the foregoing applies correspondingly. In addition, the foregoing remarks in connection with further ingredients contained in products according to the invention apply correspondingly to the further ingredients.

A method as described above, wherein the mixing or contacting of the mixture with the further ingredients takes place at a temperature that is higher than the melting point of the mixture, but is lower than 25° C., and preferably is lower than 23° C., is preferred according to the invention.

A method is further preferred for production of a mixture that is liquid at a pressure of 101325 Pa, i.e. at normal pressure, and a temperature of 20° C. or higher and comprises racemic d,l-menthol and optionally additional l-menthol, in a total amount from 72.0 through 85.0 wt. % relative to the total weight of the mixture, preferably for production of a mixture according to the invention (as described above),
with the following steps:

providing or preparing racemic d,l-menthol and optionally additional l-menthol in a total amount from 72.0 through 85.0 parts by weight, mixing the racemic d,l-menthol and optionally the additional l-menthol with:

d,l-isomenthol in an amount from 7.5 through 20.0 parts by weight, a first alkylene diol and optionally one or a plurality of further alkylene diols in a total amount from 7.0 through 11.0 parts by weight, further ingredients in a total amount from 0 through 2.0 parts by weight, wherein the parts by weight are relative to the total weight of the mixture,
wherein the proportions are adjusted so that the resulting mixture is liquid at a pressure of 101325 Pa and a temperature of 20° C. or higher.

Particularly preferably, the foregoing concerning the alkylene diol or diols used, and the amounts preferably to be used, applies correspondingly.

Accordingly, a method according to the invention (as described above) is particularly preferred, wherein the first alkylene diol or one, a plurality of or all of the alkylene diols are selected from the group consisting of alkylene glycols with 2 through 6 carbon atoms.

Particularly preferably, the or one, a plurality of or all of the alkylene diols is/are selected from the group consisting of ethylene glycol, 1,2-propylene glycol, 1,3-propylene glycol, 1,2-butylene glycol, 1,4-butylene glycol and 1,2-hexylene glycol.

A method according to the invention (as described above) is generally preferred, wherein the, one, a plurality of or all of the alkylene diols are selected from the group consisting of ethylene glycol, propylene glycol and hexylene glycol.

A method according to the invention, as described above, is particularly preferred, wherein the weight ratio of d,l-menthol to l-menthol is greater than 1:4, preferably greater than 1:2. Moreover, the above statement concerning the ratio of d,l-menthol to l-menthol applies correspondingly.

Another aspect of the present invention relates to the use of d,l-isomenthol mixed with a first alkylene diol and optionally one or a plurality of further alkylene diols as a means for lowering the melting point of d,l-menthol, optionally in the presence of additional l-menthol, preferably to a temperature of 20° C. or lower at a pressure of 101325 Pa.

In pharmaceutical products, a mixture according to the invention acts for example as a penetration enhancer. Another aspect of the present invention therefore relates to the use of a mixture according to the invention as a penetration enhancer.

The invention is explained in more detail below on the basis of examples. Unless stated otherwise, all amounts are based on weight.

EXAMPLES

1. Preparation of Mixtures According to the Invention and Comparative Mixtures and Determination of the Melting Points

1.1 General Procedure:

Preparation of the Mixtures According to the Invention or the Comparative Mixtures:

The desired amounts of d,l-menthol, l-menthol and d,l-isomenthol (see below, 1.2-1.6) are melted, put together and (while they are still in the liquid state), 1,2-propylene glycol is added.

All the following amounts are to be understood as percentages by weight, relative to the total weight of the respective mixture.

Sample Preparation for Determination of Melting Points:

After the mixture has cooled to room temperature, it is seeded with a small amount of d,l-menthol crystals and optionally the mixture is cooled until noticeable crystallization begins. Then the mixture is stored for 24 h at 5° C. in a refrigerator.

In each case approx. 1 g is taken from the mixtures as sample and placed in a round 10-g sample vessel with diameter of 1.5 cm. The sample vessels are then placed in a water bath heated to 15° C., in such a way that the sample amount is below the water level.

Determination of the Melting Points:

Over a period of 10 min, the temperature of the water bath is increased in a first step by 0.5° C. and is then held at this temperature for 30 min. Then the temperature of the water bath is increased in further steps in corresponding intervals by in each case 0.5° C. The melting point of the mixture or of the sample was defined as the temperature at which crystal residues could no longer be seen in the sample.

The following mixtures were prepared (as described above), wherein the stated melting points were measured (as described above):

1.2 Mixtures of d,l-menthol and 1,2-propylene glycol (Comparative Mixtures)

| d,l-menthol | 1,2-propylene glycol | m.p. [° C.] |
|---|---|---|
| 95 | 5 | 28 |
| 92.5 | 7.5 | 27.5 |
| 90 | 10 | 25 |

1.3 Mixtures of d,l-menthol, l-menthol and 1,2-propylene glycol (Comparative Mixtures)

| d,l-menthol | l-menthol | 1,2-propylene glycol | m.p. [° C.] |
|---|---|---|---|
| 60.8 | 34.2 | 5 | 27.5 |
| 59.2 | 33.3 | 7.5 | 24.5 |
| 57.6 | 32.4 | 10 | 23 |

1.4 Mixtures of d,l-menthol, l-menthol and d,l-isomenthol (Comparative Mixtures)

| l-menthol | d,l-menthol | d,l-isomenthol | m.p. [° C.] |
|---|---|---|---|
| 0 | 50 | 50 | 36.5 |
| 0 | 80 | 20 | 34.5 |
| 25 | 60 | 15 | 33 |
| 35 | 55 | 10 | 33.5 |
| 50 | 42 | 8 | 34 |

1.5 Mixtures of d,l-menthol, d,l-isomenthol and 1,2-propylene glycol (Mixtures According to the Invention No. 2, 3 and 5, Comparative Mixtures No. 1, 4 and 6-9)

| Mixture No. | d,l-menthol | d,l-isomenthol | 1,2-propylene glycol | m.p. [° C.] |
|---|---|---|---|---|
| 1 | 85.5 | 4.5 | 10 | 22.5 |
| 2 | 81 | 9 | 10 | 18.5 |
| 3 | 83.25 | 9.25 | 7.5 | 19.5 |
| 4 | 85.5 | 9.5 | 5 | 23 |
| 5 | 72 | 18 | 10 | 19.5 |
| 6 | 76 | 19 | 5 | 26 |
| 7 | 67.5 | 22.5 | 10 | 22 |
| 8 | 63 | 27 | 10 | 22.5 |
| 9 | 58.5 | 31.5 | 10 | 23 |

1.6 Mixtures of l-menthol, d,l-menthol, d,l-isomenthol and 1,2-propylene glycol

| l-menthol | d,l-menthol | d,l-isomenthol | 1,2-propylene glycol | m.p. [° C.] |
|---|---|---|---|---|
| 23 | 55 | 12 | 10 | 20 |
| 30 | 50 | 10 | 10 | 20 |

2. Organoleptic Assessment of Mixtures According to the Invention

2.1 Direct Comparison of a Mixture According to the Invention Versus d,l-menthol (Comparative Sample)

The following were incorporated, at a concentration of 0.05%, in a sugar paste (fondant):
(1.) d,l-menthol (comparative sample) or
(2.) a mixture according to the invention, consisting of 81 wt. % d,l-menthol, 9 wt. % d,l-isomenthol and 10 wt. % of 1,2-propylene glycol (example 1.5, No. 2).

Tasting of the sugar pastes by a trained panel resulted in a very similar assessment for both samples: typical, menthol-like, fresh. Moreover, advantageously, no disturbing notes or reduced refreshing effect were found for the sugar sample containing the mixture according to the invention.

2.2 Comparison of a Mixture According to the Invention Versus d,l-menthol (Comparative Sample) in a Flavored Finished Product In each case 0.5 wt. % of a standard toothpaste flavor (Optamint® FLO10529AA, Symrise AG, Holzminden) and
(1.) 0.5 wt. % d,l-menthol or
(2.) 0.5 wt. % of a mixture according to the invention, consisting of 81 wt. % d,l-menthol, 9 wt. % d,l-isomenthol and 10 wt. % of 1,2-propylene glycol (example 1.5, No. 2), were incorporated in a standard silica toothpaste mixture with a saccharin content of 0.2 wt. %. The toothpastes were tested in practical conditions by a trained panel. The result of the assessment was, for both samples: comparable, clean, menthol-like, strong and fresh.

3. Formulation Examples F1-F14

F1: Gel Toothpaste

|  | I (%) | II (%) | III (%) |
|---|---|---|---|
| Na-carboxymethylcellulose | 0.40 | 0.40 | 0.40 |
| Sorbitol 70%, in water | 72.00 | 72.00 | 72.00 |
| Polyethylene glycol (PEG) 1500 | 3.00 | 3.00 | 3.00 |
| Na-saccharin | 0.07 | 0.07 | 0.07 |
| Na-fluoride | 0.24 | 0.24 | 0.24 |
| p-Hydroxybenzoic acid (PHB)-ethyl ester | 0.15 | 0.15 | 0.15 |
| Peppermint oil flavor | 0.90 | 0.56 | 0.30 |
| Mixture according to the invention No. 2, 3 or 5 from example 1.5 | 0.125 | 0.50 | 0.90 |
| Silica abrasive | 11.00 | 11.00 | 11.00 |
| Silica thickener | 6.00 | 6.00 | 6.00 |
| Sodium dodecylsulphate (SDS) | 1.40 | 1.40 | 1.40 |
| Distilled water | To 100.00 | To 100.00 | To 100.00 |

F2: Toothpaste Against Plaque

|  | I (%) | II (%) | III (%) |
|---|---|---|---|
| Na-carboxymethylcellulose | 1.00 | 1.00 | 1.00 |
| Glycerol | 12.50 | 12.50 | 12.50 |
| Sorbitol 70%, in water | 29.00 | 29.00 | 29.00 |
| Na-saccharin | 0.20 | 0.20 | 0.20 |
| Na-fluoride | 0.22 | 0.22 | 0.22 |
| Azacycloheptane-2,2-diphosphoric acid, disodium salt | 1.00 | 1.00 | 1.00 |
| Bromochlorophene | 0.10 | 0.10 | 0.10 |
| Spearmint flavor | 1.00 | 0.60 | 0.20 |
| Mixture according to the invention No. 2, 3 or 5 from example 1.5 | 0.125 | 0.56 | 1.00 |
| Silica abrasive | 15.00 | 15.00 | 15.00 |
| Silica thickener | 5.00 | 5.00 | 5.00 |
| Sodium dodecylsulphate (SDS) | 1.50 | 1.50 | 1.50 |
| Distilled water | To 100.00 | To 100.00 | To 100.00 |

F3: Toothpaste Against Plaque

|  | I (%) | II (%) | III (%) |
|---|---|---|---|
| Carrageenan | 0.90 | 0.90 | 0.90 |
| Glycerol | 15.00 | 15.00 | 15.00 |
| Sorbitol 70%, in water | 25.00 | 25.00 | 25.00 |
| PEG 1000 | 3.00 | 3.00 | 3.00 |
| Na-fluoride | 0.24 | 0.24 | 0.24 |
| Tetrapotassium diphosphate | 4.50 | 4.50 | 4.50 |
| Tetrasodium diphosphate | 1.50 | 1.50 | 1.50 |
| Na-saccharin | 0.40 | 0.40 | 0.40 |
| Precipitated silica | 20.00 | 20.00 | 20.00 |
| Titanium dioxide | 1.00 | 1.00 | 1.00 |
| PHB-methyl ester | 0.10 | 0.10 | 0.10 |
| Eucalyptus-spearmint flavor | 1.00 | 0.60 | 0.20 |
| Mixture according to the invention No. 2, 3 or 5 from example 1.5 | 0.125 | 0.56 | 1.00 |
| Sodium dodecylsulphate | 1.30 | 1.30 | 1.30 |
| Distilled water | To 100.00 | To 100.00 | To 100.00 |

F4: Toothpaste for Care of Sensitive Teeth

|  | I (%) | II (%) | III (%) |
|---|---|---|---|
| Na-carboxymethylcellulose | 0.70 | 0.70 | 0.70 |
| Xanthan gum | 0.50 | 0.50 | 0.50 |
| Glycerol | 15.00 | 15.00 | 15.00 |
| Sorbitol 70%, in water | 12.00 | 12.00 | 12.00 |
| K-nitrate | 5.00 | 5.00 | 5.00 |
| Na-monofluorophosphate | 0.80 | 0.80 | 0.80 |
| PHB-methyl ester | 0.15 | 0.15 | 0.15 |
| PHB-propyl ester | 0.05 | 0.05 | 0.05 |
| Na-saccharin | 0.20 | 0.20 | 0.20 |
| Herbs flavor | 1.00 | 0.60 | 0.20 |
| Mixture according to the invention No. 2, 3 or 5 from example 1.5 | 0.125 | 0.56 | 1.00 |
| Ca-carbonate | 35.00 | 35.00 | 35.00 |
| Silica | 1.00 | 1.00 | 1.00 |
| Sodium dodecylsulphate (SDS) | 1.50 | 1.50 | 1.50 |
| Distilled water | To 100.00 | To 100.00 | To 100.00 |

F5: Toothpaste for Care of Sensitive Teeth

|  | I (%) | II (%) | III (%) |
|---|---|---|---|
| Hydroxyethylcellulose | 1.40 | 1.40 | 1.40 |
| Guar gum | 0.60 | 0.60 | 0.60 |
| Glycerol | 18.00 | 18.00 | 18.00 |
| Sorbitol 70%, in water | 12.00 | 12.00 | 12.00 |
| Na-saccharin | 0.35 | 0.35 | 0.35 |
| Colorant | 0.01 | 0.01 | 0.01 |
| PHB-methyl ester | 0.15 | 0.15 | 0.15 |
| PHB-propyl ester | 0.04 | 0.04 | 0.04 |
| Sr-chloride | 10.50 | 10.50 | 10.50 |
| Cinnamon flavor | 1.00 | 0.60 | 0.30 |
| Mixture according to the invention No. 2, 3 or 5 from example 1.5 | 0.225 | 0.56 | 1.00 |
| Precipitated silica | 15.00 | 15.00 | 15.00 |
| Silica | 1.60 | 1.60 | 1.60 |
| Sodium dodecylsulphate | 1.30 | 1.30 | 1.30 |
| Distilled water | To 100.00 | To 100.00 | To 100.00 |

F6: Mouthwash with Fluoride, Ready for Use

|  | I (%) | II (%) | III (%) |
|---|---|---|---|
| Ethanol | 7.00 | 7.00 | 7.00 |
| Glycerol | 12.00 | 12.00 | 12.00 |
| Na-fluoride | 0.05 | 0.05 | 0.05 |
| Pluronic F-127 ® (BASF, surface active substance) | 1.40 | 1.40 | 1.40 |
| Na-phosphate buffer pH 7.0 | 1.10 | 1.10 | 1.10 |
| Sorbic acid | 0.20 | 0.20 | 0.20 |
| Na-saccharin | 0.10 | 0.10 | 0.10 |
| Thymol-wintergreen flavor | 1.00 | 0.60 | 0.20 |
| Mixture according to the invention No. 2, 3 or 5 from example 1.5 | 0.125 | 0.56 | 1.00 |
| Colorant | 0.01 | 0.01 | 0.01 |
| Distilled water | To 100.00 | To 100.00 | To 100.00 |

F7: Mouthwash Concentrate Effective Against Mouth Odor

|  | I (%) | II (%) | III (%) |
|---|---|---|---|
| Ethanol, 95% | 80.00 | 80.00 | 80.00 |
| Na-cyclamate | 0.15 | 0.15 | 0.15 |
| Spearmint-thymol flavor | 3.50 | 3.50 | 3.50 |
| Colorant | 0.01 | 0.01 | 0.01 |

-continued

|  | I (%) | II (%) | III (%) |
|---|---|---|---|
| Mixture according to the invention No. 2, 3 or 5 from example 1.5 | 0.50 | 1.0 | 3.0 |
| Distilled water | To 100.00 | To 100.00 | To 100.00 |

F8: Chewing Gum, Sugar-containing

|  | I (%) | II (%) | III (%) |
|---|---|---|---|
| Chewing gum base | 21.00 | 21.00 | 21.00 |
| Glucose syrup | 16.50 | 16.50 | 16.50 |
| Glycerol | 0.50 | 0.50 | 0.50 |
| Powdered sugar | 60.45 | 60.40 | 60.30 |
| Spearmint flavor | 1.40 | 1.00 | 0.50 |
| Mixture according to the invention No. 2, 3 or 5 from example 1.5 | 0.15 | 0.60 | 1.20 |

F9: Sugar-free Chewing Gum

|  | I (%) | II (%) | III (%) |
|---|---|---|---|
| Chewing gum base | 30.00 | 30.00 | 30.00 |
| Sorbitol, powder | 38.45 | 38.40 | 38.30 |
| Palatinite | 9.50 | 9.50 | 9.50 |
| Xylitol | 2.00 | 2.00 | 2.00 |
| Mannitol | 3.00 | 3.00 | 3.00 |
| Aspartame | 0.10 | 0.10 | 0.10 |
| Acesulfame K | 0.10 | 0.10 | 0.10 |
| Emulgum/emulsifier | 0.30 | 0.30 | 0.30 |
| Sorbitol 70%, in water | 14.00 | 14.00 | 14.00 |
| Glycerol | 1.00 | 1.00 | 1.00 |
| Cinnamon-menthol flavor | 1.40 | 1.00 | 0.50 |
| Mixture according to the invention No. 2, 3 or 5 from example 1.5 | 0.15 | 0.60 | 1.20 |

F10: Chewing-gum Coated Tablets, Sugar-free
Q1: Chewing Gum Raw Paste

|  | I (%) | II (%) | III (%) |
|---|---|---|---|
| Chewing gum base | 37.00 | 37.00 | 37.00 |
| Sorbitol, powder | 50.50 | 50.50 | 50.50 |
| Aspartame | 0.20 | 0.20 | 0.20 |
| Plasticizer (Emulgum) | 0.50 | 0.50 | 0.50 |
| Acesulfame K | 0.20 | 0.20 | 0.20 |
| Sorbitol 70% in water | 5.00 | 5.00 | 5.00 |
| Glycerol | 4.00 | 4.00 | 4.00 |
| Peppermint oil flavor (Optamint ®, Symrise) | 1.60 | 1.60 | 1.60 |
| Menthol spray-dried | 1.00 | 1.00 | 1.00 |

All the ingredients of the chewing-gum raw paste (Q1) are mixed, stamped into chewing gum strands and then formed to individual chewing gum cushions. The chewing gum cushions are then wetted (gummed) in a rotary coating drum with a 40 wt. % gum arabic solution. The gummed chewing gum cushions are then coated in a rotary coating drum with mixture A (for composition see below). After sufficient drying with cold air, the coated chewing gum cushions are dried overnight. To apply the coating on the dried, coated chewing gum cushions, first 15 layers of coating solution B are applied by pan coating. In the 16th layer, a mixture of ingredient C and mixture B is applied. Then further layers are applied using mixture B, until the total weight of the coating (Q2) is about 35 wt. % of the weight of the original chewing gum cushions (Q1). In order to impart gloss to the chewing-gum coated tablets, a final treatment is carried out with a gloss agent from a mixture of equal proportions by weight of carnauba wax and beeswax. When chewed, the ready-to-use chewing-gum coated tablets produce a very clear, brilliant, fresh and novel menthol taste in the mouth.

Q2: Coating

The stated proportions by weight refer to the total mass of the coating (Q2) applied on the chewing gum cushions (Q1); the total mass of Q2 was about 35% relative to the mass of Q1.

|  | I (%) | II (%) | III (%) |
|---|---|---|---|
| Mixture A |  |  |  |
| Isomalt | 0.20 | 0 | 0 |
| Sorbitol | 0 | 0.40 | 0 |
| Mannitol | 0 | 0 | 0.80 |
| Mixture according to the invention No. 2, 3 or 5 from example 1.5 | 0.20 | 0.60 | 1.00 |
| Mixture B |  |  |  |
| Isomalt | 68.00 | 67.70 | 67.40 |
| Water | 26.7 | 26.6 | 26.5 |
| Gum arabic 40% in water (this proportion includes the amount used for gumming) | 2.50 | 2.50 | 2.50 |
| Acesulfame K | 0.05 | 0.05 | 0.05 |
| Aspartame | 0.05 | 0.05 | 0.05 |
| Titanium dioxide | 1.50 | 1.50 | 1.50 |
| Constituent C |  |  |  |
| Peppermint oil flavor (Optamint ®, Symrise) | 0.80 | 0.60 | 0.20 |

F11: Gelatin Capsule for Direct Consumption

|  | I (%) | II (%) | III (%) |
|---|---|---|---|
| Gelatin shell: |  |  |  |
| Glycerol | 2.014 | 2.014 | 2.014 |
| Gelatin 240 Bloom | 7.91 | 7.91 | 7.91 |
| Sucralose | 0.065 | 0.065 | 0.065 |
| Allura Red | 0.006 | 0.006 | 0.006 |
| Brilliant Blue | 0.005 | 0.005 | 0.005 |
| Composition of core: |  |  |  |
| Vegetable oil triglyceride | 85.0 | 80.0 | 73.0 |
| Flavor B | 4.0 | 6.0 | 10.0 |
| Mixture according to the invention No. 2, 3 or 5 from example 1.5 | 1.0 | 4.0 | 7.0 |

Flavor B has the following composition (given in each case in wt. %):

0.1% neotame powder, 0.05% aspartame, 29.3% lemon oil, 29.3% orange oil, 2.97% sucralose, 2.28% triacetin, 5.4% diethyl tartrate, 12.1% peppermint oil yakima, 0.7% ethanol, 3.36% 2-hydroxyethylmenthyl carbonate, 3.0% 2-hydroxypropylmenthyl carbonate, 0.27% vanillin, 5.5% D-limonene, 5.67% L-menthyl acetate.

The gelatin capsule, suitable for direct consumption, has a diameter of 5 mm, and the weight ratio of core material to shell material is 90:10. The capsule opens in the mouth within less than 10 seconds and dissolves completely within less than 50 seconds.

F12: Chewable Sweet

| | | |
|---|---|---|
| Water | | 7.5% |
| Sugar | Refined sugar C4 | 41.2% |
| Glucose syrup | Dextrose 40 | 36.2% |
| Hardened vegetable fat | Melting point 32-36° C. | 6.5% |
| Lecithin | Emulsifier (soya lecithin) | 0.3% |
| Gelatin | Porcine gelatin | 0.8% |
| Fondant | Type-S30 | 4.8% |
| Lemon flavor | | 0.6% |
| Mixture according to the invention No. 2, 3 or 5 from example 1.5 | | 2.1% |

Instructions for preparation:
a) leave the gelatin to swell with water (1.8 times the amount of gelatin) at 70° C. for 2 hours;
b) cook the sugar, syrup, water, fat and lecithin at 123° C.;
c) slowly mix the gelatin solution with the cooking batch;
d) stir in the mixture according to the invention and the optional colorant;
e) adjust the temperature of the resultant mass on a cooling table to approx. 70° C., then add fondant and aerate in a pulling machine for approx. 3 minutes;
f) then cut and pack the chewable sweet mass.

During consumption of the chewable sweets, a powerful menthol taste is perceived while chewing; the chewable sweets have a pleasant texture.

F13: Compressed Product, Sugar-Containing or Sugar-Free

| | | |
|---|---|---|
| Dextrose (sugar-containing) or sorbitol (sugar-free) | | 98.5-98.8% |
| Magnesium stearate | Lubricant | 1.0% |
| Mixture according to the invention No. 2, 3 or 5 from example 1.5 | | 0.2-0.5% |

Instructions for preparation: Mix all the ingredients and press in a suitable machine to form compressed products.

F14: Extrudate

| | | |
|---|---|---|
| Glucose syrup, spray-dried (DE value: 31-34) | Glucidex iT33W (company Roquette) | 60.0% |
| Maltodextrin (DE value: 17-20) | (company Cerestar) | 26.0% |
| Monomuls emulsifier | Emulsifier based on hardened palm oil; melting point: 64° C., (company Grunau) | 1.5% |
| Dextrose monohydrate (DE value: 99.5) | Dextrose, containing water of crystallization (company Cerestar) | 1.5% |
| Water | | 1.5% |
| Mixture according to the invention No. 2, 3 or 5 from example 1.5 | | 9.5% |

Instructions for preparation (see also WO 03/092412):

All the ingredients are mixed and are fed into a twin-screw extruder for one-point metering. The extrusion temperatures are between 100 and 120° C., the specific energy input is 0.2 kWh/kg. The strands emerging from the nozzle plate of the extruder, which has 1-mm holes, are chopped immediately after emerging from the nozzles by rotating blades into particles with a diameter of approx. 1 mm. The resultant granules have a menthol content of 10 wt. %.

F15: Throat Sweets with Viscous Liquid Filling (Center-Filled Hard Candy)

| | I (wt. %) | II (wt. %) |
|---|---|---|
| Mixture A (shell) (80% of the sweets) | | |
| Sugar (sucrose) | 58.12 | 49.37 |
| Glucose syrup (solids content 80%) | 41.51 | 49.37 |
| Flavor mixture from example 5 | 0.17 | 0.25 |
| Mixture according to the invention No. 2, 3 or 5 from example 1.5 | 0.10 | — |
| Lemon oil | 0.10 | 0.10 |
| Citric acid | — | 0.91 |
| Total: | 100 | 100 |
| Mixture B (core) (20% of the sweets) | | |
| High fructose maize syrup (content of solid sugars 85%, just 15% water) | 84.38 | 84.36 |
| Glycerol | 15.0 | 15.0 |
| Lecithin | 0.02 | 0.02 |
| Cinnamon oil | — | 0.32 |
| Spearmint oil | 0.28 | — |
| Capsaicin | 0.05 | — |
| Vanillyl alcohol-n-butyl ether | — | 0.10 |
| Red dye, as 5% aqueous solution | 0.20 | 0.20 |
| Vanillin | 0.07 | — |
| Total | 100 | 100 |

Based on the methods described in U.S. Pat. No. 6,432,441 (example 1 there) and in U.S. Pat. No. 5,458,894 or U.S. Pat. No. 5,002,791, sweets were produced with a viscous liquid core. Both mixtures A and B were processed separately into bases for the shell (mixture A) or the core (mixture B). The filled throat sweets obtained by co-extrusion were effective, when consumed by affected persons, against cough, sore throat and hoarseness.

F 16: Sweets ('Hardboiled Candy')

| Ingredient | I (wt. %) | II (wt. %) |
|---|---|---|
| Water | 2.75 | 2.50 |
| Sugar | 60.1 | To 100 |
| Glucose syrup | 36.9 | 36.0 |
| Maltose | — | 2.00 |
| Palm kernel oil | — | 0.80 |
| Citric acid | — | 0.25 |
| Ginseng extract | — | 0.40 |
| Blue dye | — | 0.01 |
| Spearmint oil | 0.25 | 0.35 |
| Mixture according to the invention No. 2, 3 or 5 from example 1.5 | 0.5 | 0.75 |

F17: Hair Lotion

| | % | Ingredient |
|---|---|---|
| A | q.s. | Perfume oil |
| | 1.00 | PEG-40 hydrogenated castor oil |
| B | 65.0 | Alcohol |
| | 1.0 | Panthenol |
| | 0.5 | Polyquaternium-16 |
| | 0.1 | Mixture according to the invention No. 2, 3 or 5 from example 1.5 |
| | 2.00 | (1R,2S,5R)-5-methyl-2-(propan-2-yl)cyclohexyl-N-ethyloxamate |
| | 3.00 | Pentylene glycol |
| | 27.4 | Distilled water |

F18: Hair Lotion

|   | % | Ingredient |
|---|---|---|
| A | q.s. | Perfume oil |
|   | 1.00 | PEG-40 hydrogenated castor oil |
| B | 65.0 | Alcohol |
|   | 1.0 | Panthenol |
|   | 0.5 | Polyquaternium-16 |
|   | 0.1 | Mixture according to the invention No. 2, 3 or 5 from example 1.5 |
|   | 2.00 | (1R,2S,5R)-5-methyl-2-(propan-2-yl)cyclohexyl-N-ethyloxamate |
|   | 3.00 | Pentylene glycol |
|   | 1.00 | 4-t-Butylcyclohexanol |
|   | 26.4 | Distilled water |

F19: Foot Balsam

|   | % | Ingredient |
|---|---|---|
| A | 2.0 | Ceteareth-6, stearyl alcohol |
|   | 2.0 | Ceteareth-25 |
|   | 5.0 | Cetearyl-ethyl-hexanoate |
|   | 4.0 | Cetyl alcohol |
|   | 4.0 | Glyceryl stearate |
|   | 5.0 | Mineral oil |
|   | 0.2 | Mixture according to the invention No. 2, 3 or 5 from example 1.5 |
|   | 0.5 | Camphor |
| B | 65.3 | Distilled water |
|   | q.s. | Preservative |
| C | 1.0 | Bisabolol |
|   | 1.0 | Tocopheryl acetate |
| D | 0.5 | (1R,2S,5R)-5-methyl-2-(propan-2-yl)cyclohexyl-N-ethyloxamate |
|   | 4.5 | Pentylene glycol |
|   | 5.0 | Hamamelis extract |

Instructions for preparation: Heat the ingredients according to A and B separately to about 80° C. Mix component B in component A with homogenizing. Cool to about 40° C. with stirring. Add components C and D and re-homogenize for a short time. Cool to room temperature with stirring.

F20: Foot Balsam

|   | % | Ingredient |
|---|---|---|
| A | 2.0 | Ceteareth-6, stearyl alcohol |
|   | 2.0 | Ceteareth-25 |
|   | 5.0 | Cetearyl-ethyl-hexanoate |
|   | 4.0 | Cetyl alcohol |
|   | 4.0 | Glyceryl stearate |
|   | 5.0 | Mineral oil |
|   | 0.2 | Mixture according to the invention No. 2, 3 or 5 from example 1.5 |
|   | 0.5 | Camphor |
| B | 65.3 | Distilled water |
|   | q.s. | Preservative |
| C | 1.0 | Bisabolol |
|   | 1.0 | Tocopheryl acetate |
| D | 0.5 | (1R,2S,5R)-5-methyl-2-(propan-2-yl)cyclohexyl-N-ethyloxamate |
|   | 4.5 | Pentylene glycol |
|   | 0.3 | 4-t-Butylcyclohexanol |
|   | 4.7 | Hamamelis extract |

Instructions for preparation: Heat the ingredients according to A and B separately to about 80° C. Mix component B in component A with homogenizing. Cool to about 40° C. with stirring. Add components C and D and re-homogenize for a short time. Cool to room temperature with stirring.

F21: Face Cleansing Lotion—Type O/W

|   | % | Ingredient |
|---|---|---|
| A | 10.0 | Cetearyl-ethyl-hexanoate |
|   | 10.0 | Caprylic/capric triglyceride |
|   | 1.5 | Cyclopentasiloxane, cyclohexasiloxane |
|   | 2.0 | PEG-40 hydrogenated castor oil |
| B | 3.5 | Caprylic/capric triglyceride, Na-acrylate copolymer |
| C | 1.0 | Tocopheryl acetate |
|   | 0.2 | Bisabolol |
|   | q.s. | Preservative |
|   | q.s. | Perfume oil |
| D | 3.0 | Polyquaternium-44 |
|   | 0.5 | Cocotrimonium methosulphate |
|   | 0.5 | Ceteareth-25 |
|   | 2.0 | Panthenol, propylene glycol |
|   | 4.0 | Pentylene glycol |
|   | 0.1 | Disodium EDTA |
|   | 0.3 | Mixture according to the invention No. 2, 3 or 5 from example 1.5 |
|   | 61.4 | Distilled water |

Instructions for preparation: Dissolve component A. Mix component B with component A. Incorporate component C into the combined components A and B. Dissolve component D in the combined components A, B and C and homogenize. Continue stirring for a further 15 minutes.

F22: Body Spray

|   | % | Ingredient |
|---|---|---|
| A | 3.0 | Ethyl hexyl methoxycinnamate |
|   | 2.0 | Diethylamino-hydroxybenzoyl-hexyl-benzoate |
|   | 1.0 | Polyquaternium-44 |
|   | 3.0 | Pentylene glycol |
|   | 2.0 | Panthenol, propylene glycol |
|   | 1.0 | Cyclopentasiloxane, cyclohexasiloxane |
|   | 10.0 | Octyldodecanol |
|   | 0.5 | PVP |
|   | 10.0 | Caprylic/capric triglyceride |
|   | 3.0 | $C_{12-15}$ alkyl benzoate |
|   | 3.0 | Glycerol |
|   | 1.0 | Tocopheryl acetate |
|   | 0.3 | Bisabolol |
|   | 0.2 | Mixture according to the invention No. 2, 3 or 5 from example 1.5 |
|   | 60.0 | Alcohol |

Instructions for preparation: Weigh the ingredients of component A and dissolve until clear.

F23: Skin Care Gel

|   | % | Ingredient |
|---|---|---|
| A | 3.6 | PEG-40 hydrogenated castor oil |
|   | 15.0 | Alcohol |
|   | 0.1 | Bisabolol |
|   | 0.5 | Tocopheryl acetate |
|   | q.s. | Perfume oil |
| B | 3.0 | Panthenol |
|   | 0.6 | Carbomer |
|   | 4.0 | Pentylene glycol |
|   | 0.1 | Mixture according to the invention No. 2, 3 or 5 from example 1.5 |
|   | 72.3 | Distilled water |
| C | 0.8 | Triethanolamine |

F24: Aftershave Lotion

|   | % | Ingredient |
|---|---|---|
| A | 10.0 | Cetearyl-ethyl-hexanoate |
|   | 5.0 | Tocopheryl acetate |
|   | 1.0 | Bisabolol |
|   | 0.1 | Perfume oil |
|   | 0.3 | Acrylate/$C_{10-30}$ alkyl acrylate crosspolymer |
| B | 15.0 | Alcohol |
|   | 1.0 | Panthenol |
|   | 3.0 | Glycerol |
|   | 0.3 | Mixture according to the invention No. 2, 3 or 5 from example 1.5 |
|   | 4.0 | Pentylene glycol |
|   | 0.1 | Triethanolamine |
|   | 60.2 | Distilled water |

Instructions for preparation: Mix the ingredients of component A. Dissolve component B, incorporate into component A and homogenize.

F25: After-Sun Lotion

|   | % | Ingredient |
|---|---|---|
| A | 0.4 | Acrylate/C10-30 alkyl acrylate crosspolymer |
|   | 15.0 | Cetearylethyl hexanoate |
|   | 0.2 | Bisabolol |
|   | 1.0 | Tocopheryl acetate |
|   | q.s. | Perfume oil |
| B | 1.0 | Panthenol |
|   | 15.0 | Alcohol |
|   | 3.0 | Glycerol |
|   | 0.3 | Mixture according to the invention No. 2, 3 or 5 from example 1.5 |
|   | 4.0 | Pentylene glycol |
|   | 59.9 | Distilled water |
| C | 0.2 | Triethanolamine |

Instructions for preparation: Mix the ingredients of component A. Mix component B in component A with homogenizing. Neutralize with component C with homogenizing again.

F26: Sun Lotion

|   | % | Ingredient |
|---|---|---|
| A | 4.5 | Ethyl hexyl methoxycinnamic acid |
|   | 2.0 | Diethylamino-hydroxybenzoyl-hexyl benzoate |
|   | 3.0 | Octocrylene |
|   | 2.5 | Di-C12-13 alkyl malate |
|   | 0.5 | Tocopheryl acetate |
|   | 4.0 | Polyglyceryl-3-methyl-glucose distearate |
| B | 3.5 | Cetearyl isononanoate |
|   | 1.0 | VP/eicosene copolymer |
|   | 5.0 | Isohexadecane |
|   | 2.5 | Di-C12-13 alkyl malate |
|   | 3.0 | Titanium dioxide, trimethoxycaprylyl silane |
| C | 5.0 | Glycerol |
|   | 1.0 | Sodium cetearyl sulphate |
|   | 0.5 | Xanthan gum |
|   | 56.4 | Distilled water |
| D | 0.3 | Mixture according to the invention No. 2, 3 or 5 from example 1.5 |
|   | 4.0 | Pentylene glycol |
|   | 1.0 | Phenoxy-ethanol, methyl paraben, ethyl paraben, butyl paraben, propyl paraben, isobutyl paraben |
|   | 0.3 | Bisabolol |

Instructions for preparation: Heat the ingredients according to A and B separately to about 80° C. Mix component B in component A with homogenizing. Heat component C to about 80° C. and mix into the combined components A and B with homogenizing. Cool to about 40° C. with stirring, add component D and homogenize again.

The invention claimed is:

1. A mixture consisting essentially of:
   72.0 to 85.0 wt. % racemic d,l-menthol and optionally l-menthol;
   7.5 to 20.0 wt. % d,l-isomenthol; and
   7.0 to 11.0 wt. % of a first alkylene diol and optionally one or more further alkylene diols;
   wherein the percentages by weight are relative to the total weight of the mixture, and wherein the mixture is liquid at a pressure of 101325 Pa and a temperature of 20° C.

2. The mixture as claimed in claim 1, wherein the first alkylene diol or one or more further alkylene diols are selected from the group consisting of alkylene glycols comprising 2 to 6 carbon atoms.

3. The mixture as claimed in claim 1, wherein the one or more alkylene diols are selected from the group consisting of ethylene glycol, propylene glycol and hexylene glycol.

4. The mixture as claimed in claim 1, wherein the weight ratio of d,l-menthol to l-menthol is greater than 1:4.

5. The mixture as claimed in claim 1 consisting essentially of:
   72.0 to 85.0 wt. % racemic d,l-menthol;
   7.5 to 20.0 wt. % d,l-isomenthol;
   7.0 to 11.0 wt. % 1,2-propylene glycol;
   wherein the percentages by weight are relative to the total weight of the mixture.

6. The mixture as claimed in claim 1, consisting essentially of:
   48 to 57 wt. % racemic d,l-menthol;
   21.0 to 32.0 wt. % d,l-menthol;
   8.0 to 14.0 wt. % d,l-isomenthol; and
   7.0 to 11.0 wt. % 1,2-propylene glycol;
   wherein the percentages by weight are relative to the total weight of the mixture.

7. A product comprising:
   a mixture as claimed in claim 1 and further ingredients, wherein the further ingredients do not contain menthol and/or isomenthol.

8. The product as claimed in claim 7, wherein the product is selected from the group consisting of flavoring material preparations, cosmetic preparations, preparations used for nutrition and/or pleasure, oral hygiene products, dental hygiene products, perfumes, pharmaceutical and dermatological products, encapsulated menthol-containing preparations, and household products.

9. A process for preparing a product as claimed in claim 7, comprising:
   providing or preparing a mixture consisting essentially of:
   72.0 to 85.0 wt. % racemic d,l-menthol and optionally l-menthol;
   7.5 to 20.0 wt. % d,l-isomenthol; and
   7.0 to 11.0 wt. % of a first alkylene diol and optionally one or more further alkylene diols;
   wherein the percentages by weight are relative to the total weight of the mixture, and
   wherein the mixture is liquid at a pressure of 101325 Pa and a temperature of 20° C.; and,
   mixing or contacting the mixture with further ingredients, wherein the further ingredients do not contain menthol and/or isomenthol.

10. The process as claimed in claim 9, wherein the mixing or contacting of the mixture with the further ingredients occurs at a temperature that is higher than the melting point of the mixture, but that is lower than 25° C.

11. A process for preparing a mixture as claimed in claim 1, comprising:
mixing the racemic d,l-menthol and optionally the additional l-menthol with
the d,l-isomenthol, and
the first alkylene diol and optionally one or more further alkylene diols,
wherein the proportions are adjusted within the ranges specified in claim 1 so that the resulting mixture is liquid at a pressure of 101325 Pa and a temperature of 20° C.

12. The process as claimed in claim 11, wherein the first alkylene diol or one or more further alkylene diols are selected from the group consisting of alkylene glycols comprising 2 to 6 carbon atoms.

13. The process as claimed in claim 11, wherein the one or more alkylene diols are selected from the group consisting of ethylene glycol, propylene glycol and hexylene glycol.

14. The process as claimed in claim 11, wherein the weight ratio of d,l-menthol to l-menthol is greater than 1:4.

15. A method of lowering the melting point of d,l-menthol that is optionally in the presence of additional l-menthol to a temperature of 20° C. or lower at a pressure of 101325 Pa comprising mixing d,l-menthol that is optionally in the presence of additional l-menthol with a first alkylene diol and optionally one or more further alkylene diols so as to form a final mixture consisting essentially of:
72.0 to 85.0 wt. % racemic d,l-menthol and optionally l-menthol;
7.5 to 20.0 wt. % d,l-isomenthol; and
7.0 to 11.0 wt. % of a first alkylene diol and optionally one or more further alkylene diols.

16. A penetration enhancer comprising the mixture as claimed in claim 1.

17. A product comprising a mixture as claimed in claim 1 and further ingredients, wherein the further ingredients do not contain an alkylene diol.

18. A product prepared by mixing a mixture as claimed in claim 1, or contacting a mixture as claimed in claim 1, with further ingredients, wherein the further ingredients do not contain menthol and/or isomenthol.

19. A product prepared by mixing a mixture as claimed in claim 1, or contacting a mixture as claimed in claim 1, with further ingredients, wherein the further ingredients do not contain an alkylene diol.

20. The mixture as claimed in claim 1, wherein the weight ratio of d,l-menthol to l-menthol is greater than 1:2.

* * * * *

UNITED STATES PATENT AND TRADEMARK OFFICE
CERTIFICATE OF CORRECTION

PATENT NO. : 8,496,950 B2
APPLICATION NO. : 13/302705
DATED : July 30, 2013
INVENTOR(S) : Sorge et al.

It is certified that error appears in the above-identified patent and that said Letters Patent is hereby corrected as shown below:

In the Claim

Column 24, claim 5, line 29, should read as follows:

7.5 to 20.0 wt.% d,l-isomenthol; and

Signed and Sealed this
Twelfth Day of November, 2013

Teresa Stanek Rea
*Deputy Director of the United States Patent and Trademark Office*